United States Patent [19]

Cobben

[11] Patent Number: 4,887,287
[45] Date of Patent: Dec. 12, 1989

[54] MOBILE X-RAY APPARATUS COMPRISING EXCHANGEABLE WHEELS

[75] Inventor: Johannes I. M. Cobben, Eindhoven, Netherlands

[73] Assignee: U.S. Philips Corporation, New York, N.Y.

[21] Appl. No.: 267,057

[22] Filed: Nov. 4, 1988

[30] Foreign Application Priority Data

May 6, 1988 [NL] Netherlands .......................... 8801196

[51] Int. Cl.⁴ ............................ A61B 6/00; A61B 6/10
[52] U.S. Cl. ..................................... 378/198; 378/197
[58] Field of Search .............................. 378/196–198, 378/193, 195, 208

[56] References Cited

U.S. PATENT DOCUMENTS

| 1,239,145 | 1/1914 | Wantz | 378/197 |
| 3,790,805 | 2/1974 | Foderaro | 378/198 |

FOREIGN PATENT DOCUMENTS

| 0231969 | 8/1987 | European Pat. Off. | 378/198 |
| 1074211 | 1/1960 | Fed. Rep. of Germany | 378/198 |
| 1541163 | 7/1969 | Fed. Rep. of Germany | 378/197 |
| 1105394 | 11/1955 | France | 378/198 |
| 1526087 | 5/1968 | France | 378/198 |

Primary Examiner—Carolyn E. Fields
Assistant Examiner—Joseph A. Hynds
Attorney, Agent, or Firm—Thomas A. Briody; Jack E. Haken; Jack D. Slobod

[57] ABSTRACT

For transport on rough terrain as well as on the floor of a hospital, a mobile X-ray diagnostic apparatus has exchangeable wheels which are adapted to the relevant surface. When the apparatus is transported on an uneven and soft surface, wide wheels having a large diameter can be used, while in hospital conditions narrow wheels having a small diameter can be used. In order to render the X-ray diagnostic apparatus suitable for transport on different surfaces in a simple operation, the wheels can be readily exchanged without using tools; a towbar is also provided.

9 Claims, 3 Drawing Sheets

MOBILE X-RAY APPARATUS COMPRISING EXCHANGEABLE WHEELS

BACKGROUND OF THE INVENTION

The invention relates to a mobile X-ray diagnostic apparatus, comprising a C-arc on which an X-ray source and an X-ray detector are mounted opposite one another, and also comprising two side wheels and a front wheel which can swivel about a vertical shaft.

An X-ray diagnostic apparatus of this kind is known from Applicant's prior European Patent Application EP 231 969 A1.

An apparatus described therein is mounted so as to be dismantleable on a mobile support comprising three wheels. A front wheel which can be swung up enables correct positioning of the X-ray diagnostic apparatus with respect to an object to be examined, for example a patient.

SUMMARY OF THE INVENTION

It is an object of the invention to render an X-ray diagnostic apparatus of the kind set forth also easily transportable on an uneven surface; to achieve this, the X-ray diagnostic apparatus comprises means for securing exchangeable wheels and exchangeable wheels which can be detachably connected to these means.

Displacement of a mobile X-ray diagnostic apparatus on an uneven and soft or sandy surface is facilitated by a large wheel width which prevents the X-ray diagnostic apparatus from sinking into the surface, and by a comparatively large wheel diameter which enables transport over obstacles and also keeps the lower side of the support clear of these obstacles. The X-ray diagnostic apparatus will usually be manually transported over comparatively small distances, for which purpose use is made of a towbar which can be simply connected to an attachment on the front wheel without the use of tools. During the making of X-ray exposures, the towbar can be uncoupled from the X-ray diagnostic apparatus so as not to impede the freedom of movement of the X-ray diagnostic apparatus with respect to an object to be examined. Because the towbar is attached to the swivel-type front wheel of the support of the X-ray diagnostic apparatus, obstacles can be easily circumvented. Moreover, via the towbar an upwards directed force can be exerted on a swivel axis of the suspension of the front wheel. As a result, a front arm of the X-ray diagnostic apparatus can be lifted off and the front wheel can be locked to the front arm in the correct position. The exchangeable wheels may comprise solid tires which require comparatively little maintainance, or air tires so that the wheels have a shock absorbing effect. In order to facilitate the transport of the X-ray diagnostic apparatus in graded terrain, a number of exchangeable wheels comprise a brake with an adjustable braking force, so that detrimental high downgrade speeds can be avoided. In order to enable a fast transition from the transport of the mobile X-ray diagnostic apparatus from field conditions to hospital conditions, the set of wheels for use in field conditions can be simply and quickly detached. Thus, the usually dirty terrain wheels need not enter, for example a sterile operating room.

A further preferred embodiment of the invention is characterized in that the pair of exchangeable side wheels can be secured in two positions of the support with a different wheel base. When the X-ray diagnostic apparatus is to be transported across a somewhat uneven surface, for example the floor in a depot with many obstacles, a small width of the wheel base of the support is desirable in order to avoid these obstacles, for example door posts. A smaller wheel base reduces the stability of the X-ray diagnostic apparatus, but its maneuverability increases, this is a substantial advantage on sites where many obstacles are present.

BRIEF DESCRIPTION OF THE DRAWING

The invention will be described in detail hereinafter with reference to the accompanying drawing; therein.

DETAILED DESCRIPTION OF THE PREFERRED EMBODIMENTS

Figure 1:
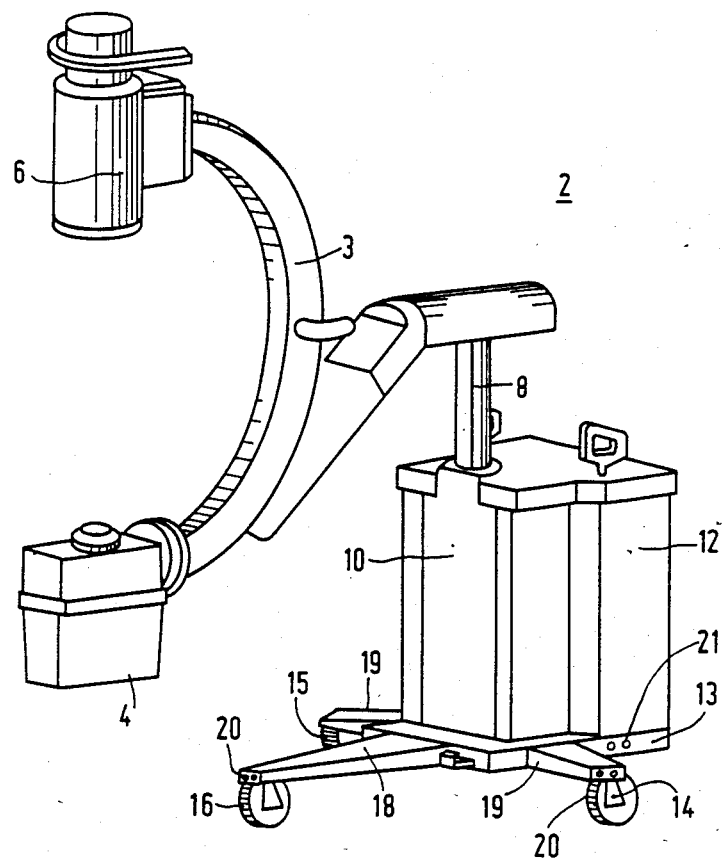
FIG. 1 is a simplified view of a mobile X-ray apparatus.

FIG. 1 shows a mobile X-ray diagnostic apparatus 2 comprising an X-ray source 4 and an X-ray detector 6 which are mounted opposite one another on a C-arc 3. The C-arc 3 is secured to a cylinder 8 which is secured in a pedestal-like portion 10 so that its height is adjustable. The pedestal-like portion 10 and an electrical module 12 are arranged on a mobile support 13 which comprises casters 14, 15 and 16. A first caster 16 is secured to a projecting arm 18 so that it can swivel. The casters 14, 15 and 16 are small and narrow wheels which are suitable for transporting the X-ray diagnostic apparatus 2 on a very even surface, for example the floor of a operating room. In an end face of the side arms 19 and in an end face of the front arm 18 there are provided pairs of holes 20 in which two projecting connection pins of the exchangeable wheels can be inserted. In the support 13 there are also provided two pairs of holes 21 which are situated in opposite positions and in which the connection pins of the exchangeable wheels can be fitted. When the exchangeable side wheels are fitted to the support 13, the wheel base of the support is smaller than when they are fitted to the side arms 19. This may be attractive in avoiding obstacles, for example door posts.

Figure 2:
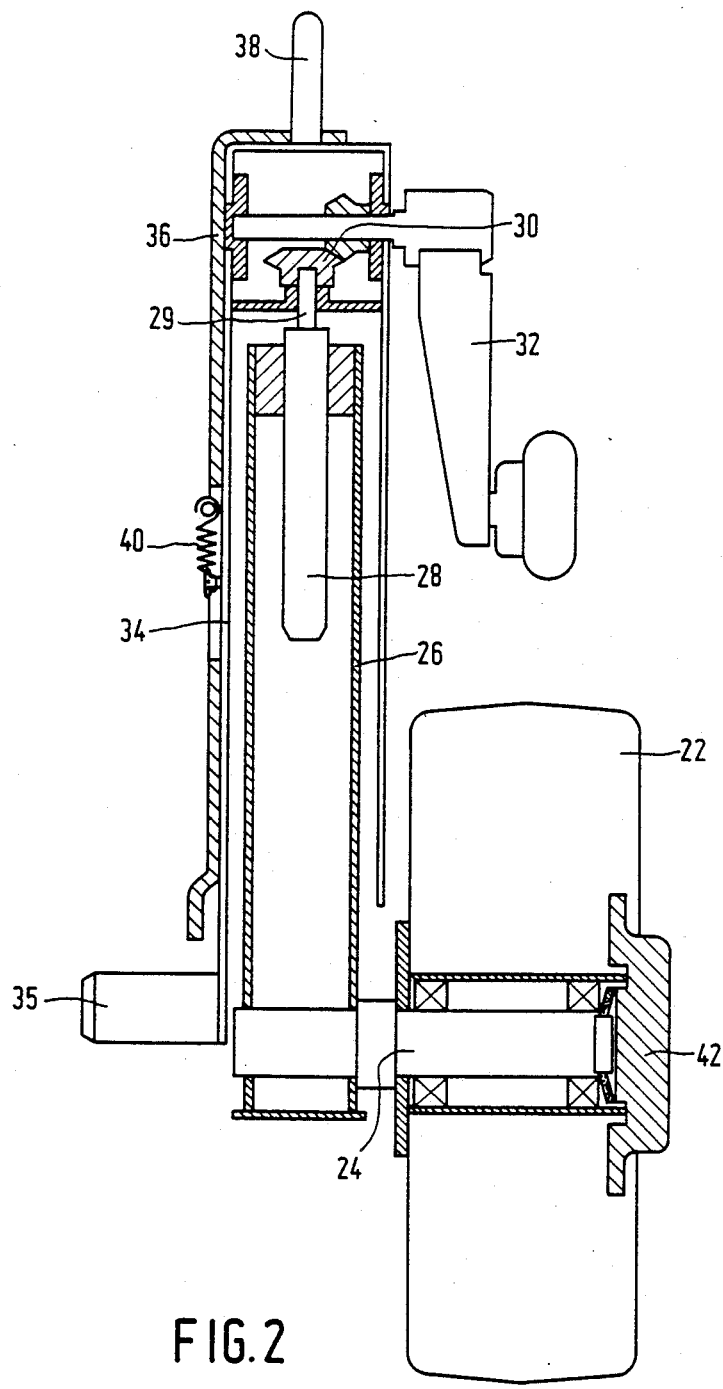
FIG. 2 is a sectional view of an exchangeable side wheel.

FIG. 2 shows an exchangeable wheel 22 which is suspended from a cylinder 26 by way of a shaft 24. A bush 28 which is secured in the cylinder 26 can be screwed around a shaft 29 of a spindle construction 30, so that the cylinder 26 is movable with respect to an enclosing cylinder 34 by rotation of an arm 32. The exchangeable wheel is to be secured to a side of the X-ray diagnostic apparatus by way of two projecting fixing pins 35 (only one of which is visible in FIG. 2) which fit in openings 22 in the end faces of the side arms 19 and in the openings 21 in the support 13. To this end, a latch 36 must be pulled upwards, using a grip 38 against the force of a spring 40. When the fixing pins 35 project far enough into the openings 20 or 21, the grip can be released and the latch 34 drops into a slot (not shown in the drawing) provided at the areas where the exchangeable wheels are attached. When the latch 36 engages a slot, the movement of the exchangeable wheel in the axial direction is blocked. Using the arm 32, the exchangeable wheel can be lowered with respect to the support 13 in order to adjust a desirable clearance between the transport surface and the support. The small and narrow side casters 14 are then lifted off the ground. Using a cap 42 which can be screwed against the shaft 24, a continuously variable braking force can be adjusted, for a wheel.

Figure 3:
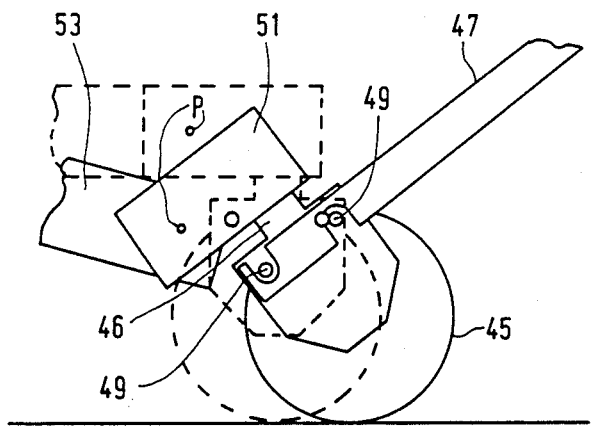
FIG. 3 diagrammatically illustrates a method of attaching the exchangeable front wheel.

FIG. 3 diagrammatically illustrates the attachment of the front exchangeable wheel 45 by means of a towbar 47. By first securing the side exchangeable wheels to the support 13 or to the side arms 19 and by increasing the distance between the support 13 and the transport surface by means of the spindle construction 39, the X-ray diagnostic apparatus is inclined slightly forwards, the front arm 18 then bearing on the small wheel 16 which is not shown in FIG. 3. The front exchangeable wheel 45 can be swivelled around a shaft P. The towbar 47 has a forked end provided with two slots in both parts thereof, which slots fit around pairs of cams 49 provided on both sides of the wheel 45. The front exchangeable wheel 45 can be tilted by means of the towbar 47 so that the shaft P is raised, part of the wheel suspension 51 then being situated in the prolongation of a second part 53 of the wheel suspension. Using a latch pin 60 (visible in FIG. 4), the part 53 can be secured in the prolongation of the part 51. The small front wheel 16 is clear of the transport surface in this position.

Figure 4:
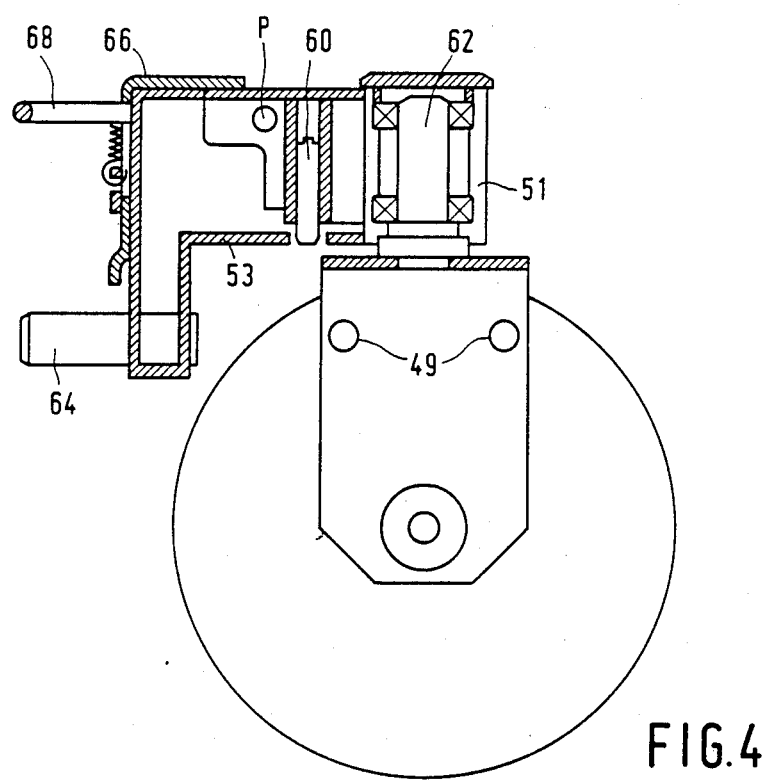
FIG. 4 is a sectional view of the exchangeable front wheel.

FIG. 4 is a side elevation of a cross-section of the front exchangeable wheeel with its suspension. The part 53 is blocked with respect to the part 51 by means of the latch pin 60. The front exchangeable wheel can swivel around a shaft 62 and can be rotated by means of the towbar by securing the towbar to the pairs of cams 49, thus enabling maneuvering of the X-ray diagnostic apparatus. The front exchangeable wheel is secured to the arm 18 (in the same way as the side exchangeable wheels) by inserting a pair of fixing pins 64 (only one of which is visible in FIG. 4) in the pair of holes 20 in the arm 18, the latch 66 then being raised by means of a grip 68. The latch 66 engages a slot in the arm 18 and inhibits movement of the front wheel in the direction of the fixing pins 64.

What is claimed is:

1. A mobile x-ray diagnostic apparatus, comprising a C-arc on which an x-ray source and an x-ray detector are mounted opposite one another, and support means for said C-arc having a first set of ground wheels including two side wheels connected to said support means at respective first spaced-apart points for swiveling around vertical axes, characterized in that the x-ray diagnostic apparatus further comprises an exchangeable second set of ground wheels including two side wheels and that said support means further comprises means for detachably securing said exchangeable second set of ground wheels to said support means at respective second spaced apart points, and means for adjusting the height of the two side wheels of said exchangeable second set relative to said respective second points to enable transferring operative support of said apparatus from the side wheels of one of said first and second sets to the wheels of the other set.

2. An X-ray apparatus as claimed in claim 1, wherein said first and exchangeable second sets of ground wheels each comprise a front wheel and wherein said apparatus further comprises a tow bar and means for securing said tow bar to a suspension of the exchangeable front wheel of the second set such that said tow bar is capable of exerting an upwards force on a generally horizontal pivot axis of the suspension and enables the X-ray diagnostic apparatus to be towed in a controllable manner.

3. An X-ray apparatus as claimed in claim 1, characterized in that an exchangeable wheel of said second set comprises a brake means with an adjustable braking force.

4. An X-ray apparatus as claimed in claim 1, wherein said first and exchangeable second sets of ground wheels each comprise a front wheel and wherein said apparatus further comprises a tow bar and means for securing said tow bar to a suspension of the exchangeable front wheel of the second set such that said tow bar is capable of exerting an upwards force on a generally horizontal pivot axis of the suspension and enables the X-ray diagnostic apparatus to be towed in a controllable manner.

5. An X-ray apparatus as claimed in claim 4, characterized in that an exchangeable wheel of said second set comprises a brake means with an adjustable braking force.

6. An X-ray apparatus as claimed in claim 1, characterized in that an exchangeable wheel of said second set comprises a brake means with an adjustable braking force.

7. An X-ray diagnostic apparatus as claimed in claim 1 wherein said respective second spaced-apart points comprise alternative differently spaced-apart points for the exchangeable two side wheels of said second set.

8. An X-ray diagnostic apparatus as claimed in claim 2 wherein said respective second spaced-apart points comprise alternative differently spaced-apart points for the exchangeable two side wheels of said second set.

9. An X-ray diagnostic apparatus as claimed in claim 3 wherein said respective second spaced-apart points comprise alternative differently spaced-apart points for the exchangeable two side wheels of said second set.

* * * * *